United States Patent [19]

Jönsson et al.

[11] 4,008,267

[45] Feb. 15, 1977

[54] 3,3'-DI(SULFONYLOXY-GROUP-CONTAINING)SUBSTITUTED BENZIDINE DERIVATIVES

[75] Inventors: Nils Ake Jönsson, Solna; Ferenc Merenyi; Lars-Erik Westlund, both of Taby, all of Sweden

[73] Assignee: AB Kabi, Stockholm, Sweden

[22] Filed: Oct. 16, 1974

[21] Appl. No.: 515,195

Related U.S. Application Data

[63] Continuation-in-part of Ser. No. 118,531, Feb. 24, 1971, Pat. No. 3,859,341.

[52] U.S. Cl. .......................... 260/509; 260/239 BE; 260/239 BF; 260/269; 260/287 R; 260/319.1; 260/465 E; 260/510; 260/518 R; 260/519; 260/558 A; 195/103.5 C
[51] Int. Cl.$^2$ ............... C07C 143/64; C07C 143/56
[58] Field of Search ........................... 260/509, 510

[56] References Cited

UNITED STATES PATENTS

| | | | |
|---|---|---|---|
| 3,496,225 | 2/1970 | Logan et al. | 260/513 T |
| 3,506,580 | 4/1970 | Rubinfeld et al. | 260/513 T |

FOREIGN PATENTS OR APPLICATIONS

| | | | |
|---|---|---|---|
| 1,313,267 | 4/1973 | United Kingdom | 260/509 |

OTHER PUBLICATIONS

Gilbert, "Sulfonation and Related Reactions" pp. 164 – 171 (1965).

*Primary Examiner*—Bernard Helfin
*Assistant Examiner*—Nicky Chan

[57] ABSTRACT

Disclosed are benzidine derivatives substituted in each of the 3,3'-positions by the substituent

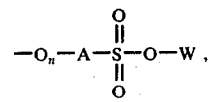

wherein W is hydrogen or an alkali metal, the subscript $n$ is zero when A is the divalent branched chain alkylene having from 2 to about 7 carbon atoms, and $n$ is one when A is straight chain divalent alkylene with 3 or 4 carbons. Also disclosed are the corresponding derivatives wherein the sulfonyl group is replaced by the carbonyl group. Further disclosed are chromogen-reactive indicator compositions having as their chromogen constituent one of the foregoing benzidine derivatives. These compositions (1) are useful to test for a substance for which there exists a specific oxygen-oxidoreductase, such as a sugar, an amino acid, uric acid, and the like, and thus (2) contain also a peroxidase, a hydrogen-peroxide-oxidoreductase, and a specific oxygen-oxidoreductase for the specific material in the testing of which the composition is to be used.

12 Claims, No Drawings

3,3'-DI(SULFONYLOXY-GROUP-CONTAINING-)SUBSTITUTED BENZIDINE DERIVATIVES

This application is a continuation-in-part of copending application Ser. No. 118,531 filed Feb. 24, 1971, now U.S. Pat. No. 3,859,341 issued Jan. 7, 1975.

This invention is that of a new class of stable compounds which are 3,3'-disubstituted benzidine derivatives. More specifically these compounds are benzidine having at both the 3- and 3'-positions the substituent group $-O_n-A-X-W$, wherein the subscript n is zero or one, A is a divalent lower alkylene chain with from 2 and beneficially 3 to about 7 carbons, X is the carbonyloxy group

or particularly the sulfonyloxy group

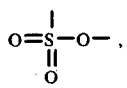

and W is hydrogen or other chromogen-reactive-indicator compatible cation (as hereinafter defined) such as an alkali metal as sodium or potassium.

These new 3,3'-disubstituted benzidine derivatives are primarily stable chromogens. They include also their chromogen-reactive-indicator compatible acid addition salts (as hereinbelow defined) of the derivatives wherein X is the carbonyloxy group, for example, their hydrogen halogenic acid addition salts such as their di-hydrohalides with any of the hydrogen halides as hydrobromic, hydrofluoric, or hydriodic acid, and particularly hydrochloric acid as in the di-hydrochloride salt of the 3,3'-disubstituted benzidine derivative, their hydrogen sulfates (from the use of sulfuric acid), or the sulfonates such as provided by use of aryl sulfonic acids as the mononuclear such acids as phenylsulfonic acid and toluenesulfonic acid, and binuclear such acids as napththalene sulfonic acid.

These 3,3'-disubstituted benzidine derivatives (including these acid addition salts) of the invention are useful as the oxidizable chromogen constituent of a chromogen-reactive-indicator composition which in addition to the chromogen comprises peroxidase and an oxygen-oxidoreductase, for example, specific to a particular organic substance, the presence of which is to be tested for and for which there exists a specific oxygen-oxidoreductase, for example, an amino acid, uric acid, pyridoxaminephosphate, or a sugar to be tested for, such as glucose oxidase or galactose oxidase. Such reactive-indicator composition is used in the well known analytical method wherein hydrogen peroxide forms during the analytical reaction and serves to act on the oxidizable chromogen (that is to say, in its reduced state) to convert it to the oxidized state wherein it provides a visible color change in the presence of the particular substance such as a sugar or other of these organic substances being tested for.

Another part of the invention is the resulting chromogen-reactive-indicator compositions containing as their chromogen constituent a 3,3'-disubstituted benzidine derivative (or acid addition salt of those wherein X is the carbonyloxy group) of the invention, along with the use of these compositions in an analytical procedure applied, for example, to a sugar by use of such chromagen-reactive-indicator composition as in the qualitative or quantitative detection of such a sugar as glucose or galactose.

In a number of such analytical methods wherein hydrogen peroxide is formed during the analytical reaction it acts on a suitable chromagen compound which in its reduced state does not absorb light in the visible range of the spectrum, to convert the chromogen to its oxidized state which does absorb visible light.

Such analytical methods are used, for example, in the assay of such an organic substance for which a specific oxygen-oxidoreductase exists, as in the assay of individual sugars such as glucose, galactose, wherein an oxidase specific for the sugar involved, that is to say, an oxygen-oxidoreductase such as glucose oxidase or galactose oxidase, acts solely on the type of sugar to be determined, with formation of hydrogen peroxide. The latter under the influence of peroxidase enzyme, that is hydrogen-peroxide-oxidoreductase, oxidizes the chromogen compound with change of color proportionate to the concentration of the sugar.

The briefly earlier above used nomenclature including the term "oxidoreductase" is in accordance with the Enzyme Commission Classification System. Accordingly, Thomas E. Burman's "Enzyme Handbook", Springer-Verlag, Berlin, Heidelberg, New York, 1969, shows that all enzymes taking part in any redox-process are called oxidoreductases. Those which catalyze the reaction wherein oxygen is an electron acceptor are called oxygen-oxidoreductases. Those which catalyze reactions wherein hydrogen peroxide is an electron acceptor are called hydrogen-peroxide-oxidoreductases.

Other similarly behaving analyses are, for example, the determination of (i) uric acid with the use of uricase, or (ii) an amino acid with the aid of the corresponding amino acid oxidase, or (iii) pyridoxaminephosphate by pyridoxaminephosphate oxidase.

Chromogen-reactive-indicators are well known in the art by their inclusion as the color change indicating constituent or chromogen in chromogen-reactive-indicator compositions widely used, for example, to impregnate test strips such as those reactive-indicator compositions comprising peroxidase, an oxidizable chromogen forming a differently colored oxidation product in the presence of the peroxidase, and an oxidase specific, for example, to a particular sugar such as glucose or galactose being tested for, as illustrated in the Arne Lennart Dahlqvist U.S. Pat. No. 3,598,704 and page 20 below.

Thus, the earlier above mentioned chromogen-reactive-indicator compatible cation is one other than hydrogen which, when present as the carboxylate- or sulfonate-forming cation in a 3,3'-disubstituted benzidine derivative of the invention, is compatible with, by being inert to, the hydrogen peroxide, the peroxidase, and the further enzyme as the oxygen-oxidoreductase, such as glucose oxidase or galactose oxidase, or uricase, pyridoxaminephosphate oxidase, or amino acid oxidase, included in the chromogen-reactive-indicator composition, and to any buffer included in the composition.

Similarly, the chromogen-reactive-indicator compatible acid addition salt of the 3,3'-disubstituted benzidine derivative of the invention is an addition salt of the specific derivative (wherein X is the carbonyloxy group) and prepared by the use of an inorganic or organic acid which when combined with the derivative to form an acid addition salt of it leaves the resulting acid addition salt compatible, in that it is inert to, the just foregoing referred to constituents of a chromogen-reactive-indicator composition.

In analytical tests of the above referred to type, certain simple benzidine derivatives, such as o-dianisidine and o-tolidine, have attained wide practical use as the chromogens. In their oxidized state light absorption occurs within the wave length range of about 450 nanometers (nm), and there is found a direct relationship between the color extinction and the amount of the sugar or other component substance to be determined.

The chromogens used heretofore, however, manifest certain disadvantages. For example, the low solubility of the earlier used benzidine derivatives, being about 100 mg./liter in the reduced state and about 10 mg./liter in the oxidized state, is a drawback. Therefore, the color that they provide must be observed and recorded within a short time span. Furthermore, the color of oxidized o-dianisidine is sensitive to light. When exposed to light, its extinction can decline quickly to the extent of up to 25 per cent, resulting in incorrect and widely varying results. The time required for the development of color at about 450 mm is disturbingly long in determinations where o-dianisidine and o-tolidine are used.

With them, at room temperature a color development time of between 50 to 60 minutes often is required. Then too, the tubing material used in the analytical instruments absorbs oxidized o-dianisidine and o-tolidine with its resulting discoloration, which in turn results in giving incorrect analytical data. To avoid the disturbingly long development time of the color which absorbs light in the same wave length range as o-dianisidine, a temporarily appearing color having an absorption at about 630 nm often is utilized with o-tolidine. Moreover, this color is very sensitive to variations in pH and temperature, which also influence the time for the maximum development of the color.

The studies carried out in the development of this invention to attain chromogens with properties suitable for the higher demands of modern analytical activity, resulted in the herein described new class of chromogen compounds meeting these demands and having the following general formula:

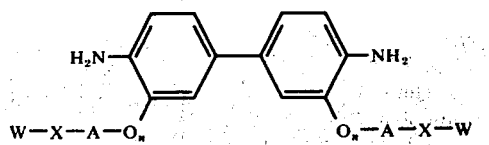

as well as their earlier herein mentioned chromogen-reactive-indicator compatible acid addition salts, and in which formula the subscript $n$ is zero or one, A is a divalent lower alkylene chain with from 2 and beneficially at least 3 to about 7 carbons, and X and W separately are defined as recited respectively earlier above (in the second paragraph of this specification). The group —X—W is the carboxyl or sulfonic acid group, or the carboxylate or sulfonate group when W is a chromogen-reactive-indicator compatible cation other than hydrogen.

The 3,3'-disubstituted benzidine derivatives, the new class of chromogens of the invention, can be obtained by various methods including different combinations of steps. Initially in each individual procedure the availability of a suitable starting material is important. In preparing the compounds of the general formula for the 3,3'-disubstituted benzidine derivatives of the invention, wherein $n$ is 1, it is beneficial, for example, to start with the commercially readily available o-dianisidine. Reference to its formula,

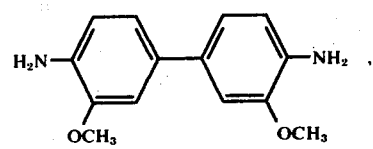

shows that by demethylation of the methoxy groups and acylation of the amino groups to block them, o-dianisidine can be converted to the corresponding diphenol. Suitable groups for blocking the amino groups are the amino-group-blocking acyl groups, for example, the acetyl, benzoyl, or phthalyl group.

Before seeking to introduce the desired side chain or substituent at the 3- and 3'-positions, the diphenol suitably should be converted into phenolate form, i.e. the diphenolate salt, preferably its sodium or potassum di-phenolate, by reaction with an alkalizing agent, for example, an alkali metal hydride such as sodium hydride, or an alkali metal alcoholate as sodium alcoholate or potassium alcoholate. Then the coupling of the desired side chain with the thus formed phenolate groups can be carried out in a suitable inert solvent such as dimethylformamide, or an alcohol, or possibly in aqueous solution. In the latter case the conversion of the hydroxyl groups to phenolate salt easily can be done with an alkali metal hydroxide.

Compounds suitable for use in introducing the desired substituent chain —$O_n$—A—X—W have the general formula Z-A-J, wherein A has its earlier above recited scope, Z is a halogen atom (e.g. chlorine, bromine, or iodine) or an arylsulfonyloxy group such as phenylsulfonyloxy, toluylsulfonyloxy, or naphthylsulfonyloxy; and when X in the general formula of the desired end product is to be carbonyloxy, then J is the carboxyl group or a group convertible to it such as the cyano group or an alkoxycarbonyl group.

In the specific case where A is dimethylene (—$CH_2$—)$_2$, the coupling can be carried out by addition of acrylonitrile. J can be, for example, a halogen atom (as earlier above exemplified) or hydroxyl. Either of them thereafter can be converted in known manner into a sulfonic acid group. Also J and Z jointly can form the sulfonyloxy group of a sultone ring such as propanesultone or butanesultone, as shown by Examples 3 part (a) and 4. Any of these cyclic esters may be alkylated on its lower alkyl portion.

Further effective compounds having the formula Z-A-J are, for example, beta-chloropropionitrile, gamma-chlorobutyronitrile, gamma-chlorobutyramide, as well as the corresponding bromo-compounds, and gamma-p-toluene sulfonyloxy butyronitrile.

After the introduction of the side chain on the phenyl rings, the blocking groups are removed from the amino groups in known manner, e.g. by hydrolysis.

By another procedure, o-dianisidine can be used as the starting material in such a way that it first is converted into 3,3'-dihydroxy-4,4'-dinitrodiphenyl. That, in the same manner as described above about the use of the compounds having the formula Z-A-J, is coupled with a such compound to provide the desired 3,3'-side chain. Thereafter the nitro groups are converted into amino groups by reduction in known manner.

In cases where the subscript n in the general formula for the end products is zero and X is the carbonyloxy group, the preparation of these products preferably starts with a lactam having the formula

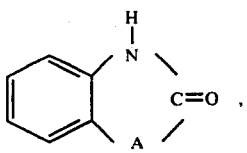

wherein A is lower alkylene of the scope earlier above stated. These lactams are obtained easily in known manner from the corresponding cyclic ketones of the formula

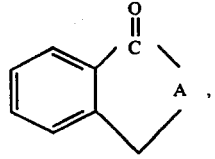

wherein A is the same as stated for the lactams. These lactams are converted by known benzene-ring halogenation into the corresponding benzo-ring-substituted halogen, beneficially iodo, derivatives having the following general formula:

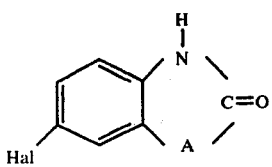

After blocking the imino group in this halogen derivative by addition of a blocking residue such as an acylic or sulfonyloxy residue, and reacting the thus blocked halogen derivative with copper (as by the Ullmann reaction), the halogen is removed from the benzene ring with resulting linking together of two of them whereby the imino-group blocked derivative is converted into the corresponding (similarly-blocked) biphenyl derivative with the following general formula:

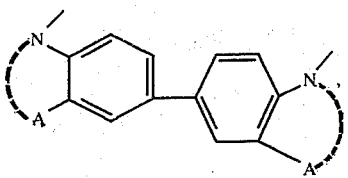

wherein A is the same as in the just preceding formula. These biphenyl derivatives (with a fused heterocyclic ring on each benzene ring) upon either alkaline or acid hydrolysis, for example, as seen in part (d) of each of Examples 5 and 6, yield the desired 3,3'-disubstituted benzidine derivative.

Illustrative products of the invention obtained by various of the disclosed methods for their preparation are shown by, but not to be restricted to, the following examples:

EXAMPLE 1

Gamma, gamma'-(4,4'-diamino-3,3'-biphenyldioxy)dibutyric acid dihydrochloride a. To a suspension of 16 grams of sodium hydride in 800 milliliters of anhydrous dimethylformamide, a total of 90 gm. of 4,4'-diacetamino-3,3'-dihydroxybiphenyl is added in small portions under agitation in a nitrogen atmosphere, following which the temperature is kept at about −5° C. by cooling in a cooling bath. The mixture is agitated for about 1 hour until the liberation of hydrogen ceases. Under continued cooling 90 gm. of methyl gamma-chlorobutyrate is added dropwise. The cooling bath then is removed and the temperature is allowed to increase to about 20° C. The introduction of nitrogen is stopped and the temperature is increased successively to 80° C. and maintained overnight. The major part of the solvent is distilled off under vacuum on a water-bath, and the residue in the flask is poured into 2 liters of ice water under agitation. After about a couple of hours, the product is decanted and thoroughly washed with water. The crude product is allowed to dry, and then is dissolved in 2 liters of boiling 2-propanol and filtered. After cooling, 110 gm. (73%) of methyl gamma,gamma'-(4,4'-diacetamino-3,3'-biphenyldioxy)dibutyrate are obtained. A sample recrystallized from 2-propanol melts at 152° to 160° C.

b. 74 gm. of this methyl ester end product of part (a) are added in portions under agitation in a nitrogen atmosphere to a solution of 27 gm. of sodium hydroxide in 450 ml. of water and 450 ml. of methanol, during which procedure the temperature is kept at 20° C. for about 20 hours and thereafter at 50° C. for 6 hours. The major part of the methanol then is distilled off under vacuum. The remaining solution is diluted with 1.5 liters of water and filtered. After further dilution with 3 liters of water, the free gamma,gamma'-(4,4'-diacetamino-3,3'-biphenyldioxy)dibutyric acid is precipitated by cautiously adding 2 N hydrochloric acid.

c. The precipitated compound is separated and washed with water. Yield 90%. The crude product is dissolved in about 750 ml. of boiling acetic acid and hot water (about 400 ml.) is added until a slight haze appears. 30 gms. of decolorizing carbon are added and the mixture agitated and filtered while hot. On cooling, the purified product crystallizes out and is filtered off and on drying yields 49.7 gm. (71%) melting at 214°–217° C.

d. 40 gm. of this purified end product of part (c) are boiled under reflux for 6 hours with 500 ml. of concentrated hydrochloric acid. The resulting crystalline paste is decanted and washed with concentrated hydrochloric acid. For purification this paste is dissolved in the necessary quantity of boiling water, and thereafter concentrated hydrochloric acid is added until crystallization begins. After cooling, the product is decanted, washed with concentrated hydrochloric acid and dried under vacuum over solid potassium hydroxide. Yield 80% dihydrochloride of gamma,gamma'-(4,4'-diamino-3,3'-biphenyldioxy)dibutyric acid. The product decomposes when heated without any defined melting point.

EXAMPLE 2

Gamma,gamma'-(4,4'-diamino-3,3'-biphenyldioxy)-dibutyric acid 0.92 gm. of the dihyrochloride end product of Example 1 are dissolved in 10 ml. of water. After cooling to room temperature, 0.32 gm. of pyridine is added, following which the free gamma,gamma'-(4,4'-diamino-3,3'-biphenyldioxy)dibutyric acid immediately starts crystallizing. The mother liquor is decanted off and the product is washed with water, and left as a greyish crystal powder, emitting water of crystallization of about 65° C. and decomposing at about 160° to 165° C.

EXAMPLE 3

Gamma,gamma'-(4,4'-diamino-3,3'-biphenyldioxy)dipropane sulfonic acid:

a. To a solution of 26.7 gm. of sodium hydroxide in 300 ml. of methanol is added 90 gm. of 4,4'-diacetamino-3,3'-dihydroxybiphenyl. After this diphenol has dissolved, there is added a suspension of 73.3 gms. of gamma-propanesultone in 200 ml. of methanol. The mixture is heated at 85° C. for 1 hour resulting in a crystalline slurry. After cooling it, the mother liquor is decanted from the product which then is washed with cold methanol. For purifying the crude disodium salt of gamma,gamma'-(4,4'-diacetamino-3,3'-biphenyldioxy)dipropane sulfonic acid, it is suspended and stirred in 500 ml. of methanol, and the latter is decanted. After drying, 108 gm. of a light brown compound are obtained, which decomposes without a defined melting point.

b. A solution of 40 gm. of the disodium salt product of part (a) of this example in 250 ml. of water is filtered through a column charged with a strong hydrogen ion-saturated ion exchanger. The filtrate free from sodium ions is boiled with 500 ml. of concentrated hydrochloric acid for 2 hours under reflux and then is evaporated until crystallization begins. After cooling, the mother liquor is decanted and the crystalline product is washed with methanol. For purification, the crude product is dissolved in 1.2 liters of boiling water, treated with decolorizing charcoal and filtered. After cooling, there crystallized out 11.7 gm. of gamma,gamma'-(4,4'-diamino-3,3'-biphenyldioxy)dipropane sulfonic acid which decomposes without a defined melting point above 300° C. Upon concentration of the filtrate, additional 8.7 gms. of product are obtained.

EXAMPLE 4

Delta,delta'-(4,4'-diamino-3,3'-biphenyldioxy)dibutane sulfonic acid

Delta-butane sultone is reacted with 4,4'-diacetamino-3,3'-dihydroxybiphenyl in the same manner as described in Example 3(a) for gamma-propane sultone, and the product obtained is hydrolyzed in the same manner as described in Example 3(b), following which delta,delta'-(4,4'-diamino-3,3'-biphenyldioxy)-dibutane sulfonic acid is obtained as colorless crystals which decompose upon heating at about 270° C.

EXAMPLE 5

Gamma,gamma'-(4,4'-diamino-3,3'-biphenyl)-dibutyric acid a. 32.2 gm. of 2-oxo-2,3,4,5-tetrahydro-1-H-1-benzazepine are dissolved in 300 ml. of glacial acetic acid. A solution of 32.5 gm. of iodine monochloride in 200 ml. of acetic acid is added under agitation. The mixture is kept for 48 hours at room temperature and is diluted with a large volume of water to precipitate the desired intermediate. The mother liquor is decanted and the precipitated intermediate product is washed with water and recrystallized from a mixture of methanol and water (in manner much like the recrystallization described on page 10 lines 18 to 22 hereof. The purfied 7-iodo-2-oxo-2,3,4,5-tetrahydro-1-H-1-benzazepine melts at 187° to 188° C.

b. 10 gms. of the 7-iodo-2-oxo-2,3,4,5-tetrahydro-1H-1-benzazepine from part (a) of this example are refluxed for 6 hours with 160 ml. of acetic anhydride. The solution is evaporated under vacuum following which a thick oil is obtained, which when admixed with methanol gives crystalline N-acetyl-7-iodo-2 oxo-2,3,4,5-tetrahydro-1-H-1-benzazepine with a melting point of 116° to 117° C. Yield 9.5 gm.

c. 9.4 gm. of this N-acetyl-7-iodo-2-oxo-2,3,4,5-tetrahydro-1-H-1-benzazepine, 100 ml. of anhydrous dimethyl formamide and 20 gm. of copper powder are agitated under reflux for 3 hours. Then 20 more gm. of copper powder are added and the mixture is heated and agitated for another 12 hours. The resulting solid substance is filtered off and washed with dimethyl formamide. The combined filtrate and washings are evaporated under vacuum to a small volume. After addition of water, 4.6 gm. of a solid compound are obtained, which is dissolved in a 50% mixture of methanol and water. The solution is filtered, some sodium hydroxide solution is added, following which contaminations are precipitated, and filtered off. Addition of 2 N hydrochloric acid to the filtrate precipitates out of it 7,7'-bis(2-oxo-2,3,4,5-tetrahydro-1-H-1-benzazepine) as colorless crystals which after transformation decompose at about 178° C. without any defined melting point above 300° C.

d. 1 gm. of this 7,7'-bis-benzazepine derivative from part (c) of this example is heated with 140 gm. saturated barium hydroxide solution for 7 hours at 150° C. in an autoclave. After cooling, an aqueous solution of sodium carbonate is added in a slight excess over that needed to precipitate all of the barium. The precipitated barium carbonate is filtered off and the gamma,gamma'-(4,4'-diamino-3,3'-biphenyl)dibutryic acid is precipitated from the filtrate by addition of acetic acid to about pH 5. The product decomposes without a defined melting point at about 120° C.

EXAMPLE 6

Delta,delta'-(4,4'-diamino-3,3'-biphenyl)divaleric acid a. When 2-oxo-1,2,3,4,5,6-hexahydro-1-benzazocine is used in place of the 2-oxo-2,3,4,5-tetrahydro-1-H-1-benzazepine of part (a) of Example 5 and in an equivalent amount, in the same manner there is obtained instead 8-iodo-2-oxo-1,2,3,4,5,6-hexahydro-1-benzazocine with melting point 207°–208° C.

b. Then using this 8-iodo-benzazocine derivative of part (a) of this example in place of the 7-iodo-2-oxo-benzazepine derivative starting material of part (b) of Example 5, by its same procedure there is obtained N-acetyl-8-iodo-2-oxo-1,2,3,4,5,6-hexahydro-1-benzazocine.

c. By using an equivalent amount of this N-acetyl-8-iodo-2-oxo-1,2,3,4,5,6-hexahydro-1-benzazocine of part (b) of this example in place of the corresponding N-acetyl-8-iodo-2-oxo-benzazepine product of part (c) of Example 5 and following its procedure, there is obtained instead 8,8-bis(2-oxo-1,,3,4,5,6-hexahydro-1-benzazocine).

d. 10 gm. of this 8,8'-bis(2-oxo-1,2,3,4,5,6-hexahydro-1-benzazocine) are refluxed for 12 hours with 200 ml. of concentrated hydrochloric acid. The solution is evaporated to a small volume, diluted with water, following which the pH is adjusted to 5 to 6 by adding concentrated sodium acetate solution. The precipitated delta,delta'-(4,4'-diamino-3,3'-biphenyl)divaleric acid is filtered off and washed with water yielding a greyish crystal powder which readily discolors in the air and decomposes without any defined melting point.

The end products of each of Examples 2, 3(b), 4, 5(d) and 6(b), and any other such 3,3'-(di-lower alkanoic acid- or disulfonic acid)-substituted benzidine derivative can be converted to the respective dicarboxylates or disulfonates, i.e. where W is a cation other than hydrogen, by stirring the carboxylic or sulfonic acid product in an amount of an aqueous solution (sufficient to allow suitable agitation) of, for example, an alkali metal, such as sodium or potassium, hydroxide sufficient to neutralize the quantity of the carboxylic or sulfonic acid product. The resulting respective dicarboxylate or disulfonate then is separated, for example, by carefully evaporating the aqueous solution to allow the product to crystallize out or to dryness if necessary.

The concentrated hydrochloric acid used to prepare the dihydrochloride acid addition salt as of Example 1(d) can be replaced by some other acid used with any modification in reaction conditions as may be needed to be made for its use to produce some other desired acid addition salt of that 3,3'-disubstituted benzidine derivative or any of the others produced by variations in the reactants. For example, other acid addition salts may be prepared by using sulfuric acid or an organic sulfonic acid whether aliphatic such as methylene sulfonic acid or mononuclear aromatic as benzene sulfonic acid or alkyl-substituted mononuclear as toluene sulfonic acid, or binuclear as naphthalene sulfonic acid.

It is understood that the specific starting material or reactants used in any of the foregoing examples can be replaced by others effective to provide in the end product any desired variations within the nature of the substituent —$O_n$—A—X—W in the 3-position of each benzene ring to provide further end products having a different constitution for that substituent within the scope disclosed and claimed for such end products.

For example, the methyl gamma-chlorobutyrate of Example 1 part (a) may be replaced by some other lower alkyl gamma-halobutyrate such as ethyl gamma-bromobutyrate to form the corresponding ethyl gamma,gamma'-(4,4'-diacetoamino-3,3'-biphenyldioxy)-dibutyrate. So also, gamma-bromobutyronitrile can be used and provides instead gamma,gamma'-(4,4'-diacetoamino-3,3'-biphenyldioxy)dibutyronitrile melting at 246° C., but this intermediate subsequently would need to be hydrolyzed to convert the nitrile groups to carboxyl.

In addition, any of the reagents used in carrying out certain of the reactions such as (i) the blocking of the 4,4'-diamino groups or the imino group as in the benzazepine or benzazocine starting material can be replaced by some other compatible blocking or acylating agent for blocking the activity of a reactive hydrogen of an amino or imino group, or (ii) the hydrolysis steps used in some of the examples.

The derivatives of the general formula of this invention, wherein X is the sulfonyloxy group and n is zero are illustrated by, but not restricted to, the following examples:

EXAMPLE 7

Beta,beta'-(4,4'-diamino-3,3'-biphenyl)-diethane sulfonic acid is prepared by the following steps:

a. N,N'-4,4'-biphenyldi(sulfamoylacetic) acid:

To a stirred solution of benzidine (40.4 g. 0.2 mole) in a mixture of pyridine (100 ml.) and dioxane (200 ml.) is added dropwise at about 10° C. a solution of methyl chlorosulfonylacetate (80 g. 0.46 mole) in dioxane (100 ml.). The mixture is stirred for 1 hour at room temperature and poured into 1.5 liters of water. The resulting solid precipitate is collected and added to a 10% aqueous solution of sodium hydroxide (250 ml.) and refluxed for 3 hours. The resulting clear solution is cooled and acidified to about pH 1.5 with dilute hydrochloric acid to precipitate the N,N'-4,4'-biphenyldi(-sulfamoylacetic) acid. The solid precipitate is collected, dissolved in boiling glacial acid, and water admixed to induce crystallization from the resulting aqueous acetic acid to provide 72 g. of crystals that decompose without definite melting point at about 200° C.

b. 6,6'-bi-(3,4-dihydro-4-oxo-2,1-benzothiazine-2,2-dioxide

The foregoing N,N'-4,4'-diphenyldi(sulfamoylacetic-)acid (43 g., 0.1 mole) in 200 g. of polyphosphoric acid (prepared by heating a mixture of 340 g. of $P_2O_5$ and 140 g. of 85% phosphoric acid to about 175° C.) is heated to 125° C. and maintained at this temperature for 5 minutes (with agitation by shaking the flask). After cooling, the mixture is poured into 1 liter of ice water. The resulting solid product is filtered off and crystallized from glacial acetic acid to provide off-white crystals of 6,6'-bi-(3,4-dihydro-4-oxo-2,1-benzothiazine-2,2-dioxide) decomposing without definite melting point at about 250° C.

(c) 6,6'-di-(2,1-benzothiazine-2,2-dioxide) (6,6-bisulfostyril)

The foregoing diketo compound (39.2 g., 0.1 mole), phenylhydrazine (25 g.), 95 % ethanol (500 ml.) and concentrated hydrochloric acid (1 ml., as catalyst) are refluxed for 3 hours and then concentrated to about 200 ml. Water (1 liter) is admixed and the precipitated solid dihydrazone is filtered off, washed with water and air dried. To a slurry of the crude dihydrazone in hot 95 % ethanol (2 liters) solid sodium methoxide (30 g.) is added. After the strong reaction has subsided, enough water is added to dissolve the solid precipitate and the solution is refluxed over night to complete the reaction. After concentration to a small volume, the mixture is acidified to below pH 3 with concentrated hydrochloric acid and the resulting solid precipitate collected, washed with water, air dried (at room temperature) and crystallized from glacial acetic acid as 6,6'-di-(2,1-benzothiazine-2,2-dioxide) melting at 200° to 210° C.

d. 6,6'-bi-(3,3'4,4'-tetrahydro sulfostyril)

6,6'-bisulfostyril (10 g.) in 95% ethanol (250 ml.) is hydrogenated 5 kg/cm$^2$ using 300 m.g. of a 10% palladium-on-carbon catalyst. The theoretical amount of hydrogen is rapidly taken up. The catalyst is filtered off and the solution concentrated until the product crystallized out. It is filtered off, washed with 95% ethanol, and air dried, providing an almost quantitive yield of 6,6'-bi-(3,3',4,4'-tetrahydro sulfostyril) melting at 195°–200° C.

e. Beta,beta'-(4,4'-diamino-3,3'-biphenyl)diethane sulfonic acid 6,6'-bi-(3,3'4,4'-tetrahydro sulfostyril) (25 g.) is refluxed for 24 hours with a mixture of concentrated hydrochloric acid (250 ml.) and glacial acetic acid (250 ml.). The solution is evaporated to dryness and the product is crystallized from boiling water to produce almost colorless crystals decomposing at about 250° C. without definite melting point.

The disodium salt of the product of Example 7 is obtained when a solution of 5 g. of that acid in 100 ml. of water is admixed with the calculated amount of sodium hydroxide (as a 10% aqueous solution) and the resulting solution is concentrated almost to dryness. Colorless crystals, which decompose without definite melting point, are obtained by crystallization from 9% ethanol. The dipotassium salt, prepared similarly, likewise decomposes, without definite melting point.

The reactions in liquid media in parts (c) to (e) and in preparing the alkali metal salts are preferably conducted under agitation as in part (a) as by mechanical stirring.

The content of page 15 lines 21 to 27 above applies likewise to Example 7. Thus, for example, the methyl chlorosulfonylacetate of Example 7 part (a) can be replaced by the corresponding lower alkyl (preferably with up to 7 carbons) ester such as ethyl or propyl chlorosulfonylacetate or chlorosulfonylpropionate or chlorosulfonylbutyrate to yield the corresponding intermediate product of that part (a) such as N,N'-4,4'-biphenyldi(sulfamoylpropionic) acid or N,N'-4,4'-biphenyldi(sulfamoylbutyric) acid, and like higher biphenyldi(sulfamoylalkanoic) acid, each alkanoic moiety of which having up to about 7 carbons.

Each such further N,N'-4,4'-biphenyldi(sulfamoylalkanoic) acid can be the starting material for the part (b) of Example 7 to yield its corresponding second intermediate product. Each such latter second intermediate then can be the starting material for part (c) of this Example to yield its corresponding third intermediate. Each such third intermediate can be the starting material for part (d) of Example 7 to yield its corresponding fourth intermediate. Finally, each such fourth intermediate can be the starting material of part (e) of Example 7 to yield its corresponding end product gamma,gamma'-(4,4'-diamino-3,3'-biphenyl)-dipropane sulfonic acid or other such -dialkane sulfonic acid having up to about 7 carbons in each of its alkane moieties.

The corresponding alkali metal salts (such as sodium or potassium) of each such end product dialkane sulfonic acid can be prepared in the same manner as each such alkali metal salt of the end product of Example 7 is prepared.

Any of the products that were air dried of any of the parts of Example 7 instead can be dried at 100° C. in a drying oven.

The utility of the 3,3'-disubstituted products of this invention as chromogen compounds is the basis of a further part of this invention, namely, chromogen-reactive-indicator compositions useful in analytical procedures such as those described earlier above. These compositions comprise as their chromogen constituent a 3,3'-disubstituted benzidine derivative of this invention, a hydrogen-peroxide-oxidoreductase as which peroxidase is used, a specific oxygen-oxidoreductase for the specific material in the testing for which such composition of this invention will be used, such as glucose oxidase when testing for glucose, galactose oxidase in testing for galactose, uricase in making determinations of uric acid, pyridoxaminophosphate oxidase in determining pyridoxaminophosphate, and the specific amino acid oxidase in making determinations of a specific amino acid. These three essential constituents generally are dissolved in distilled water, in which usually also is included a buffer to pH 7.

In connection with this composition portion of the invention, laboratory tests were conducted by a standard method for evaluating different chromogens. Glucose was used as the control or test substance to be tested for in these tests. Hence, its corresponding specific oxidase, namely glucose oxidase, was included as the specific oxidase in the respective chromogen-reactive-indicator compositions tested, wherein the specific constituents were included in the following standard quantitative contents:

| | |
|---|---|
| Chromogen used | 0.2 mM (i.e. millimolar), |
| peroxidase | 300 units, |
| glucose oxidase | 3000 units, |
| phosphate buffer to pH 7 | 0.1 M, and |
| distilled water to make | 1000 ml. |

Stock or test solutions were prepared containing glucose in concentrations of 25, 50, 100, 200, 300, and 400 mg. per 100 ml.

When routinely using reagents or testing compositions according to the just above described plan, determinations of biological, protein-containing materials, for example, blood, also are made. In such cases, initially a precipitation of proteins is made, for example, with 0.33 M gylcine-buffered perchloric acid to pH 2.7, after which the sample is diluted 1 part to 21. Before the final determination, this thus diluted solution is diluted further 1 part to 11 with the just described chromogen reagent solution. Thereafter the development of color is measured at 450 mm.

When this particular dilution pattern is applied to the foregoing stock or test stem solutions, finally diluted solutions with the following respective glucose contents are obtained: 2.2, 4.3, 8.6, 13.0, and 17.3 mg. per liter.

The chromogen-reactive-indicator compositions of the invention, and the improved testing method involving their use are illustrated by, but not restricted to, the following examples:

EXAMPLE A

| Chromogen used | Wave length range in nm | pH value | Solubility at pH 7 in mg/liter reduced (uncolored) | Solubility at pH 7 in mg/liter oxidized (colored) | Extinction decrease % after irradiation 5 min. under 10 Watt tungsten lamp | Time for color development in minutes 25° C | Time for color development in minutes 37° C | Absorption by tubing material |
|---|---|---|---|---|---|---|---|---|
| o-dianisidine | 450 | 6.5 | 110 | 10 | 26 | 50 | 35 | + |
| o-tolidine | 430 | 6.5 | 130 | 7 | 1 | 60 | 45 | + |
| o-tolidine | 630 | 4.5 | 130 | 7 | unstable | 10 | 6 | + |
| Product of Example 1(d) | 450 | 6.5 | 70000 | 700 | 2 | 25 | 15 | − |
| Product of Example 3(b) | 450 | 6.5 | 12000 | 120 | 2 | 25 | 15 | − |

Chromogen Of Example 1(d)

A chromogen-reactive-indicator preparation of the foregoing standard constitution with 0.2 mM gamma,-gamma'-(4,4'-diamino-3,3'-biphenyldioxy)dibutyric acid —di—HCl of Example 1(d) as a chromogen was evaluated by the foregoing standard protocol against the various glucose stock solutions. Maximum color development at 450 nm occurred within 25 minutes at 25° C. and within 15 minutes at 37° C. respectively. The solubility in water of this acid addition salt used as the new chromogen was very good, and no precipitation of chromogen occurred. Its color stability at its extinction maximum enabled reading at an optional time up to 4 hours.

For use in automatic analyzers, it is desirable that the rubber or various plastic materials forming part of the tubing should not be discolored by the chromogen-containing reagent solution. Samples of various kinds of tubings were immersed for 25 hours separately respectively in chromogen-reactive-indicator reagent compositions of the foregoing constitution, one of them having as its chromogen the product of Example 1(d) hereof, a second of them having the product of Example 3(b), and a third having o-dianisidine instead. The tube samples immersed in the reagent composition containing the product of Example 1(d) remained colorless whereas those tube samples immersed in the reagent composition containing the o-dianisidine turned brown. As to these latter, to the extent that reactions occurred between the o-dianisidine and the tube material, analyses using it yield incorrect results.

EXAMPLE B

Chromogen of Example 3(b)

A chromogen-reactive-indicator reagent preparation of the foregoing standard constitution with 0.2 mM. gamma,gamma'-(4,4'-diamino-3,3'-biphenyldioxy)dipropane sulfonic acid of Example 3(b) as its chromogen was evaluated by the foregoing standard procedure against the various glucose stock solutions. Maximum color development at 430 to 450 nm occurred within 25 minutes at 25° C. The solubility in water of the new chromogen is quite good, and thus no precipitation of it occurs. The color stability of this chromogen of Example 3(b) at extinction maximum enables reading at an optional time up to 4 hours, which was the longest period over which the test material was observed.

Like analytical tests of the compounds of the other examples show that these properties exhibited by the two chromogens of Examples 1(d) and 3(b) are manifested also by the other chromogens embraced by the general formula covering the compounds of this invention. Comparisons of the behavior of the commonly used benzidime derivatives o-dianisidine and o-tolidene with the chromogens of these examples of this invention show results given in the following table:

Except for the solubility data, the rest of the information in the foregoing table applies to each of the different chromogens identified in its first column as included separately respectively as the chromogen in a chromogen-reactive-indicator reagent preparation qualitatively and quantitatively composed as given at page 20 lines 17 to 23 above.

While the invention has been explained by detailed description of certain specific embodiments of it, it is understood that various modifications and substitutions may be made in any of them within the scope of the appended claims which are intended also to include equivalents of the disclosed specific embodiments.

What is claimed is:

1. A 3,3'-disubstituted benzidine derivative having the general formula

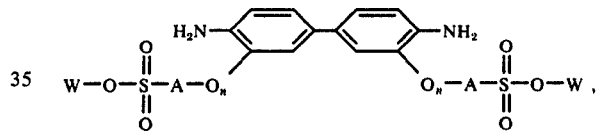

wherein (i) W is hydrogen or an alkali metal, and (ii) the subscript n is zero or one and zero when A is a divalent alkylene chain from 2 to about 7 carbons, and n is one when A is straight chain trimethylene or tetramethylene.

2. The 3,3'-disubstituted derivative as claimed in claim 1, wherein $n$ is one.

3. The 3,3'-disubstituted derivative as claimed in claim 2, wherein W is hydrogen.

4. The 3,3'-disubstituted derivative as claimed in claim 2, wherein A is straight chain trimethylene.

5. The 3,3'-disubstituted derivative as claimed in claim 4, which is gamma,gamma'-(4,4'-diamino-3,3'-biphenyldioxy)dipropane sulfonic acid.

6. The 3,3'-disubstituted derivative as claimed in claim 2, wherein A is straight chain tetramethylene.

7. The 3,3'-disubstituted derivative as claimed in claim 6, which is delta,delta'-(4,4'-diamino-3,3'-biphenyldioxy)dibutane sulfonic acid.

8. The 3,3'-disubstituted derivative as claimed in claim 1, wherein $n$ is zero.

9. The 3,3'-disubstituted derivative as claimed in claim 8, which is beta,beta'-(4,4'-diamino-3,3'-biphenyl)-diethane sulfonic acid.

10. An alkali metal salt of the 3,3'-disubstituted derivative as claimed in claim 1.

11. The sodium or potassium salt of the 3,3'-disubstituted derivative as claimed in claim 1.

12. Disodium beta,beta'-(4,4'-diamino-3,3'-biphenyl)diethane sulfonate.

* * * * *

UNITED STATES PATENT AND TRADEMARK OFFICE
CERTIFICATE OF CORRECTION

PATENT NO. 4,008,267

DATED February 15, 1977

INVENTOR(S) Nils Åke Jönsson, Ferenc Merényi and Lars-Erik Westlund

It is certified that error appears in the above-identified patent and that said Letters Patent are hereby corrected as shown below:

Col. 1, line 30, "hvdrogen" should read -- hydrogen --. Col. 2, line 54, "page 20 below" should read -- column 12 lines 29-60. Col. 3, line 29, "450 mm" should read -- 450 nm. --. Col. 3, lines 39-40, "diansidine" should read -- dianisidine --. Col. 7, line 30, the second "of" should read -- at --. Col. 8, line 28, "page 10 lines 18 to 22" should read -- column 6 lines 63-68 --. Col. 8, line 28, "purfied" should read -- purified --. Col. 8 line 32, "1H-1-benzazepine" should read -- 1-H-1-benzazepine --. Col. 8, line 36, "N-acetyl-7-iodo-2 oxo-" should read -- N-acetyl-7-iodo-2-oxo- --. Col. 8, line 61, the comma after "autoclave" should be a period. Col. 9, line 21, "8,8-bis(2-oxo -1,,3,4,5,6-hexahydro-1-"should read -- 8,8'-bis(2-oxo-1,2,3,4,5, 6-hexahydro-1- --. Col. 10, line 28, "a" should read -- (a) --. Col. 10, line 45, "b." should read -- (b) --. Col. 10, line 60, after "fostyril)" add a semicolon. Col. 11, line 10, entire line should read "(d) 6,6'-bi-(3,3',4,4'-tetrahydro sulfostyril):". Col. 11, line 12, before "5" insert -- at --. Col. 11, line 20, "e." should read -- (e) --. Col. 11, line 22, "6,6'-bi-(3,3' 4,4'-tetrahydro" should read -- 6,6'-bi-(3,3',4,4'-tetrahydro --. Col. 11, line 42, "page 15 lines 21 to 27" should read -- column 9 lines 61-68 --. Col. 12, line 58, after "just" insert -- above --. Col. 12, line 60, "450 mm." reads -- 450 nm. --.

UNITED STATES PATENT AND TRADEMARK OFFICE
CERTIFICATE OF CORRECTION

PATENT NO. 4,008,267

DATED February 15, 1977

INVENTOR(S) Nils Åke Jönsson, Ferenc Merényl and Lars-Erik Westlund

It is certified that error appears in the above-identified patent and that said Letters Patent are hereby corrected as shown below:

Col. 13, line 69, "benzidime" should read -- benzidine --. Col. 14, line 21, "page 20 lines 17 to 23" should read -- column 12 lines 35 to 44 --. Claim 1 (column 14 line 45) after "and" insert -- is --. Claim 1 (column 14 line 41, after "chain" insert -- of --.

Signed and Sealed this

Sixteenth Day of January 1979

[SEAL]

Attest:

RUTH C. MASON
*Attesting Officer*

DONALD W. BANNER
*Commissioner of Patents and Trademarks*